United States Patent [19]

McKenna

[11] 4,063,561

[45] Dec. 20, 1977

[54] DIRECTION CONTROL DEVICE FOR ENDOTRACHEAL TUBE

[75] Inventor: Roger DeSalvo McKenna, Los Angeles, Calif.

[73] Assignee: The Signal Companies, Inc., Beverly Hills, Calif.

[21] Appl. No.: 724,284

[22] Filed: Sept. 20, 1976

Related U.S. Application Data

[63] Continuation-in-part of Ser. No. 607,270, Aug. 25, 1975, abandoned.

[51] Int. Cl.² .................... A61M 25/00; A61B 17/52
[52] U.S. Cl. .................... 128/351; 128/1.3; 128/2 M
[58] Field of Search ............ 128/351, 348–350, 128/1.3, 1.4, 2 M, 8

[56] References Cited

U.S. PATENT DOCUMENTS

| 2,638,096 | 5/1953 | Waldhaus | 128/348 |
| 3,043,309 | 7/1962 | McCarthy | 128/348 |
| 3,225,767 | 12/1965 | Smith | 128/351 |
| 3,794,041 | 2/1974 | Frei et al. | 128/1.3 X |
| 3,913,565 | 10/1975 | Kawahara | 128/351 X |

FOREIGN PATENT DOCUMENTS

1,482,481  5/1967  France ................................ 128/8

Primary Examiner—Stephen C. Pellegrino
Attorney, Agent, or Firm—Donald W. Canady

[57] ABSTRACT

An endotracheal intubation device is disclosed for manipulating the lower end of an endotracheal tube into the trachea or windpipe by magnetically displacing the tip of the tube to direct it towards the trachea as the tube is lowered down a patient's throat.

9 Claims, 12 Drawing Figures

DIRECTION CONTROL DEVICE FOR ENDOTRACHEAL TUBE

RELATED APPLICATIONS

This application is a continuation-in-part of my corresponding application Ser. No. 607,270, filed Aug. 25, 1975, now abandoned.

BACKGROUND OF THE INVENTION

During surgery, surgical recovery and in other critical medical situations in which the respiratory capability of a patient is diminished, breathing-assist through a tube inserted into the trachea is often desirable. According to present medical practice, the lower end of an endotracheal tube is inserted through the throat and into the trachea by an anesthesiologist employing a laryngoscope or by medical personnel trained specifically in intubation methodology. The endotracheal tube is specifically designed for insertion into the trachea or windpipe and must be flexible for the purpose of easy manipulation and tapered at one end to facilitate insertion between the vocal cords. Even though the endotracheal tube is specially designed for easy manipulation through the throat into the trachea, such insertion of the tube into the trachea normally requires the services of a skilled anesthesiologist, since without direct visualization of the vocal cords, the tube tends to enter the esophagus because of the posterior anatomical location of the entry to the esophagus relative to the entry to the trachea and the curvature of the wall of the oropharynx.

Emergency situations frequently arise in which the insertion of an endotracheal tube is vital and life saving. In such situations it would be advantageous for an unskilled physician, nurse, or paramedic to be able to insert the endotracheal tube into the patient's trachea for breathing-assist.

Accordingly, it is an object of my present invention to provide a safe endotracheal intubation device which can be operatively inserted by a relatively unskilled technician, nurse, or physician.

It is also an object of my present invention to provide an endotracheal tube, the lower tip of which may be displaced for easy manipulation and installation into the trachea by an external magnetic device exerting an attractive force upon the tip of an endotracheal tube in which a magnetic substance is incorporated.

A prime object of my present invention is to provide a flexible magnetically responsive endotracheal intubation tube tip.

It is a further object of my invention to provide a method for intubation of an endotracheal tube.

SUMMARY OF THE INVENTION

The present invention provides a means for magnetically displacing the lower end of an endotracheal tube so that it can be readily inserted into a patient's trachea by a relatively unskilled physician, nurse, or technician. The displacement means requires the location of a ferromagnetic substance adjacent the lower tip of the endotracheal tube and either permanent or an electromganetic device which is applied externally at that portion of the patient's neck or throat to create a magnetic field for displacement of the tube tip anteriorly to permit entry of the tip into the trachea as the endotracheal tube is lowered down through the patient's throat. The manner in which the tip of the endotracheal tube is rendered magnetically responsive to the electromagnetic device is extremely important to the successful use of this intubation device.

DESCRIPTION OF THE PREFERRED EMBODIMENTS

Figure 1:
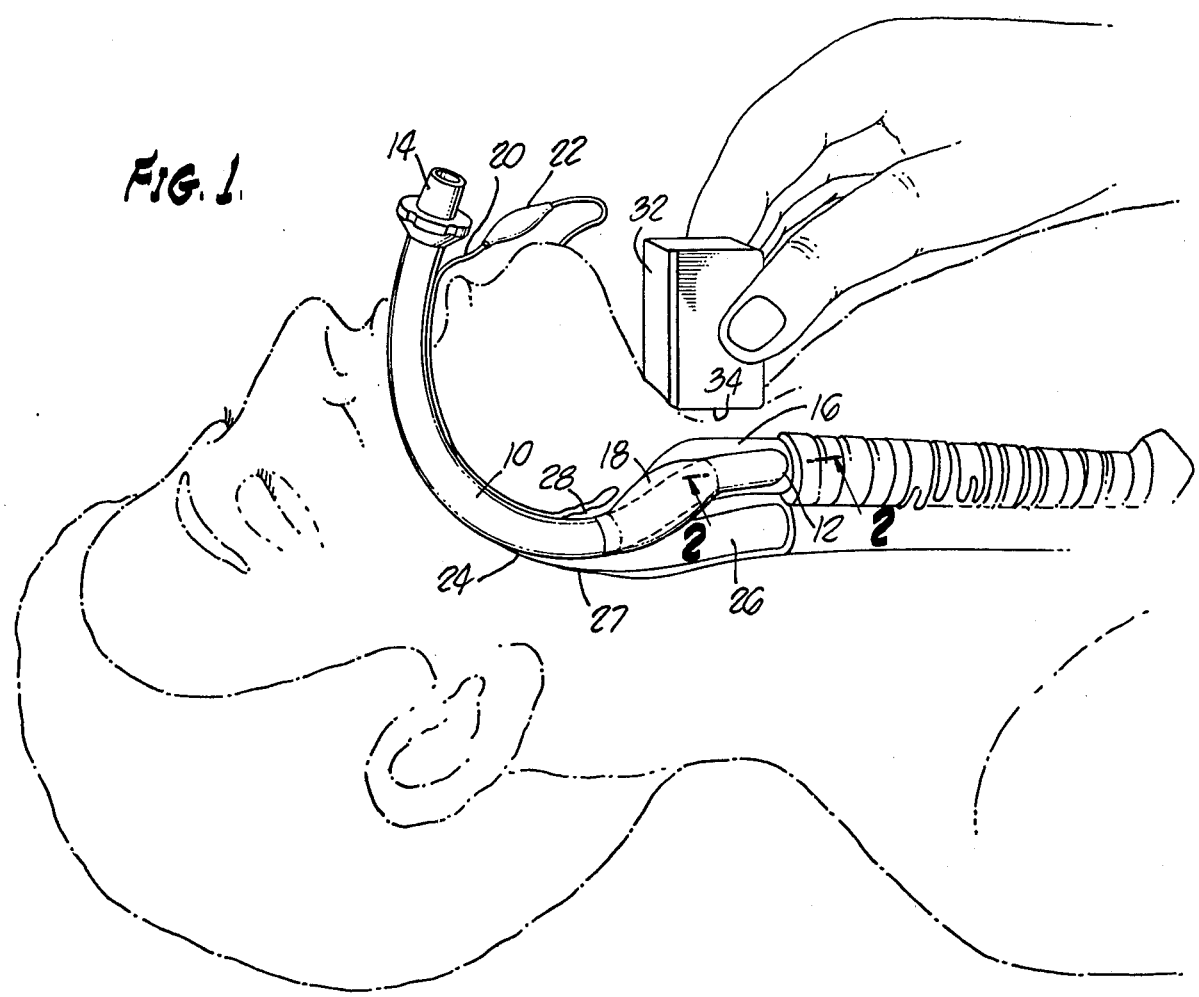
FIG. 1 is a schematic view of a patient with an endotracheal tube in accordance with the present invention, inserted into the proximal end of the trachea.

An endotracheal tube of the type used with my present invention is shown in FIG. 1 and consists of a hollow, flexible, plastic tube 10 with the insertion end tapered and bevelled for effective insertion into a human trachea through various anatomical obstacles, as discussed below. References herein to the tapered end 12 of the tube 10 refers to either the end 12 being tapered or beveled or both. The other end of the tubular member 10 shown in FIG. 1 is equipped with an adaptor 14 which is connecticle to breathing-assist equipment and which also provides a handle or grip for manipulation of the endotracheal tube through the patient's throat.

FIG. 1 shows tube 10 operatively positioned in a patient's trachea 16 for breathing-assist. The endotracheal tube 10 is equipped with a conventional inflatable seal 18 near the tapered end of the endotracheal tube which is inflatable with air through a tube syringe 20. The inflatable seal 18 is inflated with air after intubaion, to seal to exterior of the endotracheal tube 10 within the trachea and prevent passage of gastrointestinal contents, blood, mucus, etc. into the trachea around the tube as it holds the tracheal orifice open. The seal 18 is inflated by the externally positioned syringe bulb 22. Similar endotracheal tube structure is illustrated in U.S. Pat. No. 3,565,079.

The tube 10 is inserted into the patient's throat 24, as shown, and would tend to enter the esophagus 26 because of the posterior location of the esophagus opening 27 directly below the bottom of the throat 24. To cause the tapered tip 12 of the endotracheal tube 10 to deviate from this probable path into the esophagus and instead pass immediately posterior to the epiglottis 28 into the tracheal orifice, requires manipulation of the lower end of the tip 12 as it is lowered down through the patient's throat. Such manipulation of the end-tracheal tube into the trachea is normally performed only by a specially trained physician, most frequently an anesthesiologist.

Figure 2:
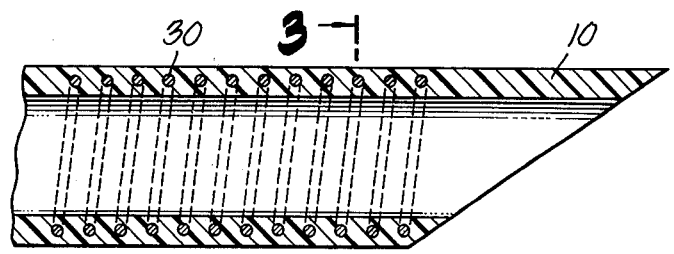
FIG. 2 is an enlarged cross-sectional view of the endotracheal tube shown in FIG. 1, taken on line 2—2 of FIG. 1.
Figure 3:
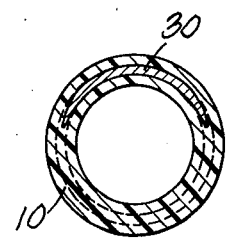
FIG. 3 is a sectional view taken on line 3—3 of FIG. 2.
Figure 6:
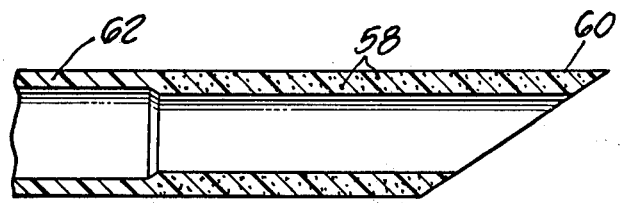
FIG. 6 is an enlarged cross-sectional view of a modified form of the tube tip used with my present invention.

The endotracheal tube shown in the drawings herein and designed in accordance with my present invention, contains a ferromagnetic element or substance embedded in the lower end of the tube 10 near the tip 12, for example a metallic element 30 best shown in FIG. 2. Element 30, in the form of a coil spring is embedded in the plastic material of the tube so that it cannot have a chemical effect upon the patient. The magnetic element may also be in the form shown in FIGS. 4 or 11, or the tube tip portion may be rendered magnetically responsive by embedding minute magnetic particles in the tube end as shown in FIG. 6 and described hereinafter.

An exterior magnetic device 32 is positioned on the anterior portion of the throat during the intubation procedure, to magnetically attract the ferromagnetic tip of the endotracheal tube and thus permit manipulation of the tube into the tracheal opening in accordance with my present invention.

Figure 7:
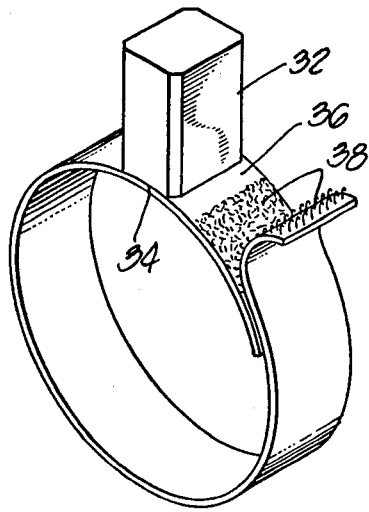
FIG. 7 shows a modified form of my present invention showing the external magnet device attached to a strap.
Figure 9:
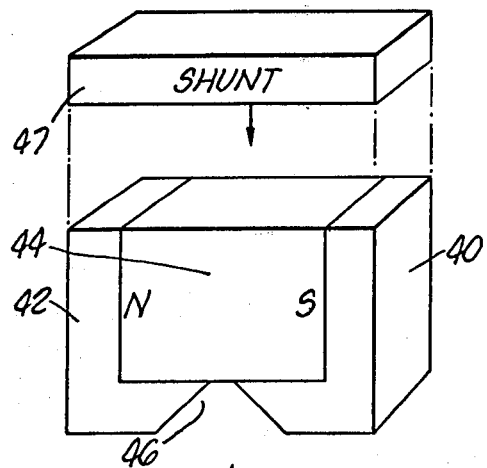
FIG. 9 shows schematically, a modified external magnetic device adapted for use in accordance with an embodiment of my present invention.

The lower surface 34 of magnetic device 32 is preferably of a concave shape or as shown in FIG. 9, to conform to the surface of the patient's throat. The exterior magnet may be manually adjustable, as shown in FIG. 1, or it may be fastened to a neck band 36, as shown in FIG. 7. The band 36 may be placed on the patient's throat adjacent the location of the tracheal opening and firmly attached to the neck by any convenient fastener, e.g. a Velcro fastener 38.

FIG. 9 shows a typical magnet design for the external magnet device which may be used on my present invention. The magnet shown in FIG. 9 is a permanent magnet conventionally made from a relatively high magnetic permeability material such as a silicon steel, cobalt, nickel or an alloy thereof. As shown in FIG. 9, the pole portions 40 and 42 surround the central magnetic core 44 and are shaped on the underside so that the magnetic field is intensified at the concave opening 46, which rests on the throat of the patient. The top of the magnet shown in FIG. 9 is provided with a shunt 47.

Figure 8:
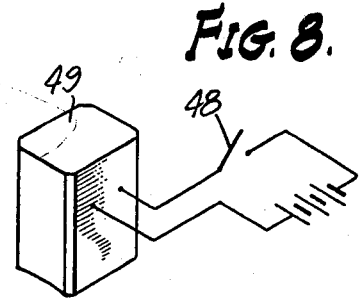
FIG. 8 shows schematically, an electromagnetic circuit which may be used with the external magnet shown in FIGS. 1 and 7.

FIG. 8 schematically shows a modification of my present invention in which the exterior magnetic device 49 is an electromagnet consisting of an insulated wire surrounding a core of soft iron (not shown) so that magnetism may be induced temporarily in the core by current flow through the wire in the circuit shown schematically. A significant advantage of an electromagnetic device is that magnetism which is induced temporarily in the core, will disappear almost immediately upon discontinuance of the current flow when the switch 48 is opened.

Figure 11:
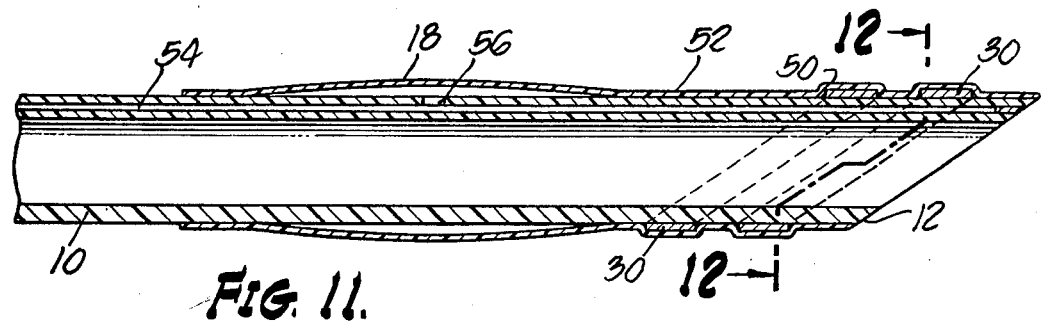
FIG. 11 is an enlarged cross-sectional view of a further modification of the tube tip of my present invention.
Figure 12:
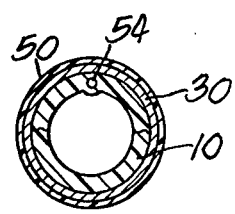
FIG. 12 is a sectional view taken on line 12—12 of FIG. 11.

The magnetically responsive element or substance which is embedded in the tip of the endotracheal tube may take one of several forms as illustrated in FIGS. 2, 4, 6, 10 and 11. It is essential to cover or embed the magnetic element or substance in the tip portion of the tube to prevent direct contact between the metallic element and the patient. Hence, the metallic element is either embedded in the tube tip, preferably by integrally forming the tube around the metallic element 30, or covering the metallic element with a layer of plastic material, as shown in FIG. 11.

Figure 4:
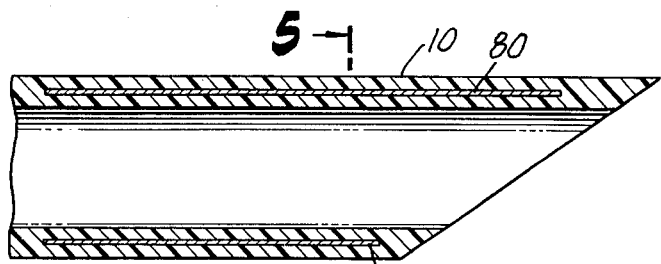
FIG. 4 is an enlarged cross-sectional view of the tip of an endotracheal tube in accordance with a modification of my present invention.
Figure 5:
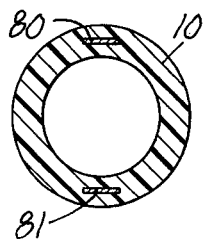
FIG. 5 is a sectional view of the apparatus shown in FIG. 4, taken on line 5—5 of FIG. 4.

In accordance with my invention, the tip of the endotracheal tube is renderd magnetically responsive without diminishing the longitudinal flexibility or maneuverability of the tip portion. This is accomplished by inserting or embedding a longitudinally flexible metallic element into the tip. A preferred embodiment utilizes a coiled ferromagnetic wire or spring 30 such as is shown in FIG. 2. or a flexible strip of ferromagnetic material 80 as shown in FIGS. 4 and 5. The embodiment shown in FIG. 10 utilizes two or more spaced-apart rings of ferromagnetic material which retains the flexibility in the tip end portion. The use of a magnetic element or substance of a length sufficient to magnetize a substantial portion of the tube near the tip, improves the maneuverability and control of the tube during intubation.

Figure 10:
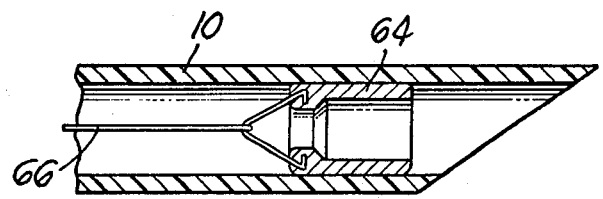
FIG. 10 is an enlarged sectional view showing a modified form of my present invention.

FIG. 10 illustrates another embodiment of my present invention, wherein the magnetically responsive element in the tube tip is a removable plug 64 (obturator) which may be withdrawn through the endotracheal tube 10 after it has been employed to magnetically displace the lower end of the endotracheal tube for intubation into the tracheal orifice. The removable magnetic plug 64 is removable from the endotracheal tube by withdrawing the wire 66, which is attached to the plug 64, as shown in FIG. 5.

In the embodiment shown in FIG. 6, the tip end of the endotracheal tube is formed with magnetically responsive substance 58 embedded in the plastic material of the tip, by conventional powder metallurgical techniques. The magnetic substance embedded within the tip end 60 of the endotracheal tube 62 shown in FIG. 6 renders the end of the tube magnetically responsive to the externally positioned magnetic device 32.

In FIG. 11, the metallic elements 70 and 72 are shown surrounding the tube near the tip thereof. A sleeve of inert plastic material is then placed or formed over the entire tip end of the endotracheal tube. Since the inflatable sealing bag 18 is normally located near the tip of the endotracheal tube, the encapsulating layer 52 for the metal rings 70 and 72 may be an integral portion or extension of the bag 18.

The air line or syringe 20 extends through the tubular member as air passageway 54 which permits inflation of bag 18 through an opening 56 in the tube wall, by pumping the syringe bag 22, in accordance with conventional practice.

In accordance with my invention, the tip end 12 of the endotracheal tube 10 is inserted through the patient's thraot 24 and when the tip portion, which is bevelled, as shown, to pass between the vocal cords, reaches the area of the epiglottis, the external magnetic device 32 is placed on the patient's throat to displace the tip end of the endotracheal tube forward in the throat so that further lowering of the endotracheal tube through the patient's throat will cause the tip end of the endotracheal tube to enter the tracheal orifice 18 rather than follow a pathway into the esophagus 26. When an electromagnet is used, the magnet may be emplaced prior to insertion of the tube tip, and the electro-magnet energized by closing switch 48 as the tip end 12 reaches the tracheal opening.

Although I have described my present invention with a certain degree of particularity with reference to certain specific embodiments, it is to be understood that the scope of my invention should not be limited to the details set forth hereinabove, but should be afforded the full scope of the appended claims.

I claim as my invention:

1. An endotracheal intubation device comprising:
   a. a flexible non-metallic tubular member with an open end tapered for insertion into a patient's trachea,
   b. flexible means embedded in the wall of the tapered end of said tubular member for rendering said end magnetically responsive; and
   c. a magnetic device externally positionable over the throat of said patient proximate to the tracheal orifice and adapted to displace said magnetically responsive end forward over the tracheal orifice as said tubular member is inserted through said patient's throat.

2. The apparatus of claim 1 wherein said flexible means is a magnetically responsive elongated member helically embedded in said tube proximate said tip.

3. The apparatus of claim 1 wherein said flexible means comprises a ferromagnetic metal strip embedded longitudinally in said tip end of said tubular member to permit transverse movement of said tip in response to said external magnetic deivce.

4. The apparatus of claim 1 wherein said magnetic device is an electromagnet.

5. The apparatus of cliam 1, including means for holding said external magnetic device in position anteriorly of said throat.

6. The apparatus of claim 1 wherein said tapered end is impregnated with a ferrogmagnetic material in granulated powder form.

7. The apparatus of claim 1 wherein said flexible means comprises a plurality of spaced apart ferromagnetic rings proximate the tip of said tubular member.

8. The apparatus of claim 1 wherein said flexible means is embedded in said tip end by affixing said flexible means into said tip and covering said affixed flexible means with a layer of flexible non-metallic material.

9. The apparatus of claim 1 wherein said means for rendering said end magnetically responsive is a removable ferromagnetic plug positionable in said tubular member proximate said tip.

* * * * *